(12) United States Patent
Hahn et al.

(10) Patent No.: US 12,053,313 B2
(45) Date of Patent: Aug. 6, 2024

(54) IDENTIFICATION OF IMPLANTED ELECTRODE LOCATION

(71) Applicant: Cardiac Pacemakers, Inc., St. Paul, MN (US)

(72) Inventors: Stephen J. Hahn, Shoreview, MN (US); Allan Charles Shuros, St. Paul, MN (US); Keith L. Herrmann, Minneapolis, MN (US); Deepa Mahajan, North Oaks, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 357 days.

(21) Appl. No.: 17/489,460

(22) Filed: Sep. 29, 2021

(65) Prior Publication Data
US 2022/0015723 A1   Jan. 20, 2022

Related U.S. Application Data

(63) Continuation of application No. 16/204,793, filed on Nov. 29, 2018, now Pat. No. 11,134,902.
(Continued)

(51) Int. Cl.
*A61B 6/12*     (2006.01)
*A61B 6/00*     (2024.01)
(Continued)

(52) U.S. Cl.
CPC .......... *A61B 6/12* (2013.01); *A61B 6/547* (2013.01); *A61B 34/25* (2016.02); *A61N 1/0565* (2013.01);
(Continued)

(58) Field of Classification Search
CPC .......... A61B 6/12; A61B 6/547; A61B 34/25; A61N 1/0565; A61N 1/3622; A61N 1/37247; A61N 1/39622; A61N 1/0563
See application file for complete search history.

(56) References Cited

U.S. PATENT DOCUMENTS 5,690,690 A    11/1997   Nappholz et al.
5,722,416 A *  3/1998    Swanson ............. A61B 5/6858
                                              600/509
(Continued)

FOREIGN PATENT DOCUMENTS

DE    102009025247    12/2010
EP         3731929    11/2020
(Continued)

OTHER PUBLICATIONS

File History for U.S. Appl. No. 16/204,793 downloaded Oct. 27, 2021 (276 pages).
(Continued)

*Primary Examiner* — Oommen Jacob
(74) *Attorney, Agent, or Firm* — Pauly, DeVries Smith & Deffner LLC

(57) ABSTRACT

A medical device system has a medical device interface configured to download data from an implanted medical device. Memory stores electrode location identification rules and display definitions. Each of the display definitions correspond to possible electrode placement locations of the implanted medical device. Processing circuitry is configured to compare the downloaded data from the implanted medical device to the electrode location identification rules to identify one or more actual electrode placement locations of the possible electrode placement locations of the implanted medical device. A user output interface is in communication with the processing circuitry. The processing circuitry is configured to cause the output to display the one or more actual electrode placement locations.

20 Claims, 12 Drawing Sheets

Related U.S. Application Data

(60) Provisional application No. 62/610,363, filed on Dec. 26, 2017.

(51) Int. Cl.
*A61B 34/00* (2016.01)
*A61N 1/05* (2006.01)
*A61N 1/362* (2006.01)
*A61N 1/372* (2006.01)
*A61N 1/39* (2006.01)

(52) U.S. Cl.
CPC ........ *A61N 1/37247* (2013.01); *A61N 1/0563* (2013.01); *A61N 1/3622* (2013.01); *A61N 1/39622* (2017.08)

(56) References Cited

U.S. PATENT DOCUMENTS

| | | | | |
|---|---|---|---|---|
| 7,177,689 | B2* | 2/2007 | Ternes | A61N 1/3684 |
| | | | | 607/28 |
| 9,572,990 | B2* | 2/2017 | Gunderson | A61B 5/318 |
| 9,707,401 | B2* | 7/2017 | Thakur | A61N 1/36578 |
| 10,729,898 | B2* | 8/2020 | Shuros | A61N 1/371 |
| 11,134,902 | B2 | 10/2021 | Hah et al. | |
| 2002/0042632 | A1* | 4/2002 | Laizzo | A61B 5/06 |
| | | | | 607/27 |
| 2003/0083711 | A1* | 5/2003 | Yonce | A61N 1/36843 |
| | | | | 607/27 |
| 2006/0116747 | A1* | 6/2006 | Eick | A61N 1/056 |
| | | | | 607/122 |
| 2007/0162082 | A1* | 7/2007 | Ternes | A61N 1/3684 |
| | | | | 607/28 |
| 2009/0234415 | A1* | 9/2009 | Sambelashvili | A61N 1/365 |
| | | | | 607/25 |
| 2009/0262992 | A1 | 10/2009 | Markowitz et al. | |
| 2011/0054559 | A1* | 3/2011 | Rosenberg | A61N 1/368 |
| | | | | 607/28 |
| 2013/0053916 | A1* | 2/2013 | Sambelashvili | A61N 1/3686 |
| | | | | 607/27 |
| 2013/0172954 | A1* | 7/2013 | Yu | A61B 5/366 |
| | | | | 607/25 |
| 2014/0155947 | A1* | 6/2014 | Kroll | A61N 1/0563 |
| | | | | 607/4 |
| 2015/0317448 | A1 | 11/2015 | Razavi et al. | |
| 2015/0342466 | A1 | 12/2015 | Thakur et al. | |
| 2016/0030747 | A1* | 2/2016 | Thakur | A61N 1/36578 |
| | | | | 607/18 |
| 2017/0263021 | A1 | 9/2017 | Ben-Haim | |
| 2019/0192092 | A1 | 6/2019 | Hahn et al. | |
| 2022/0015723 | A1* | 1/2022 | Hahn | A61B 6/12 |

FOREIGN PATENT DOCUMENTS

| | | |
|---|---|---|
| WO | 2010057063 | 5/2010 |
| WO | 2019133181 | 7/2019 |

OTHER PUBLICATIONS

"International Preliminary Report on Patentability," for PCT Application No. PCT/US2018/063378 mailed Jul. 9, 2020 (7 pages).

"International Search Report and Written Opinion," for PCT Application No. PCT/US2018/063378 mailed Feb. 22, 2019 (10 pages).

"Response to Communication Pursuant to Rules 161(1) and 162 EPC," for European Patent Application No. 18821880.4 filed Feb. 4, 2021 (13 pages).

* cited by examiner

IDENTIFICATION OF IMPLANTED ELECTRODE LOCATION

This application is a continuation of U.S. Utility application Ser. No. 16/204,793, filed Nov. 29, 2018, which claims the benefit of U.S. Provisional Application No. 62/610,363, filed Dec. 26, 2017, the content of which is herein incorporated by reference in its entirety.

FIELD OF THE TECHNOLOGY

The current technology generally relates to an implanted electrode. More particularly, the current technology relates to identification of an implanted electrode location.

BACKGROUND

Implanted cardiac rhythm management (CRM) devices can be used to restore cardiac function that has been impaired by various conditions. Some CRM devices have implanted electrodes that are surgically positioned at target locations in a patient's heart, such that electrical pulses generated by the CRM device flow through the electrodes to produce a heartbeat. Programmers are used to program and re-program the CRM devices, and such programmers and/or other monitoring devices collect and report data from the CRM devices for review by healthcare providers. The data can include cardiac data that is reported in an electrocardiogram (EGC) or in other formats.

Historically, electrodes of a CRM device are positioned at standard locations based largely on the type of therapy administered. As such, the CRM devices themselves, programmers, monitoring devices, and ECGs often assume electrode placement at those standard locations. Recently, physicians are finding that placing CRM electrodes at alternate locations in a patient's heart may achieve more desirable outcomes, but such alternate placements can result in confusion related to programming adjustments and reading ECG data.

SUMMARY

Some embodiments of the technology disclosed herein relate to a medical device system. The medical device system has a medical device interface configured to download data from an implanted medical device. Memory stores electrode location identification rules and display definitions. Each of the display definitions correspond to possible electrode placement locations of the implanted medical device. Processing circuitry is configured to compare the downloaded data from the implanted medical device to the electrode location identification rules to identify one or more actual electrode placement locations of the possible electrode placement locations of the implanted medical device. A user output interface is in communication with the processing circuitry. The processing circuitry is configured to cause the output to display the one or more actual electrode placement locations.

In some embodiments, the downloaded data comprises patient physiological data, and the user output interface is configured to display a graphical representation of the downloaded data. In some such embodiments, the downloaded data further comprises electrode location data and the processing circuitry is configured to interpret the electrode location data using the electrode location identification rules. Additionally or alternatively, the electrode location identification rules is an algorithm to correlate the morphology of the physiological data with actual electrode placement locations, and the processing circuitry is configured to compare the patient physiological data to the algorithm. Additionally or alternatively, the processing circuitry is configured to identify an actual electrode placement location as His bundle.

Additionally or alternatively, the user output interface is configured to label the graphical representation of the downloaded data as His bundle data. Additionally or alternatively, the system has a user input interface in communication with the processing circuitry, where the user input interface is configured to receive actual electrode placement locations of the implanted medical device upon implantation, and the processing circuitry is configured to cause the medical device interface to upload the actual electrode placement locations to the implanted medical device upon receiving actual electrode placement locations by the user input interface.

Additionally or alternatively, the memory is configured to store possible programming options corresponding to various electrode placement locations, where the processing circuitry is further configured to identify actual programming options of the possible programming options based on the actual electrode placement locations, and cause the user output interface to display the actual programming options consistent with the one or more actual electrode placement locations. Additionally or alternatively, the downloaded data reflects the type of implantable medical device and the processing circuitry is configured to launch an application on the system based on the downloaded data, and the processing circuitry is further configured to cause the output to display the actual electrode placement locations by modifying the launched application. Additionally or alternatively, the downloaded data can reflect the type of implantable medical device, and wherein the type of implantable medical device and the one or more actual electrode placement locations define an application to launch on the system.

Some of the embodiments of the technology disclosed herein relates to a method. A medical device interface downloads data from an implanted medical device. Lead location identification rules and display definitions are stored in memory, where each of the display definitions correspond to possible electrode placement locations of the implanted medical device. Processing circuitry compares the downloaded data from the implanted medical device to the electrode location identification rules to identify one or more actual electrode placement locations of the possible electrode placement locations of the implanted medical device. The processing circuitry causes a user output interface to display the one or more actual electrode placement locations.

In some embodiments, a graphical representation of the downloaded data is displayed that includes patient physiological data on the user output interface. Additionally or alternatively, processing circuitry interprets electrode location data using the electrode location identification rules, where the downloaded data further comprises the electrode location data. Additionally or alternatively, the processing circuitry compares the patient physiological data to the electrode location identification rules that comprise an algorithm to correlate morphology of the data with actual electrode placement locations. Additionally or alternatively, the processing circuitry identifies an actual electrode placement location as His bundle.

Additionally or alternatively, a user output interface labels the graphical representation of the downloaded data as His bundle data. Additionally or alternatively, a user input interface receives actual electrode placement locations of the implanted medical device upon implantation, and the processing circuitry causing the medical device interface to upload the actual electrode placement locations to the implanted medical device upon receiving actual electrode placement locations by the user input interface.

Additionally or alternatively, possible programming options corresponding to various electrode placement locations are stored in the memory and the processing circuitry identifies actual programming options of the possible programming options based on the actual electrode placement locations. The processing circuitry causes the user output interface to display the actual programming options consistent with the one or more actual electrode placement locations. Additionally or alternatively, the processing circuitry launches a particular application on system hardware based on the type of implantable medical device, and modifies the labels in an output of the application to reflect the one or more actual electrode placement locations. Additionally or alternatively, processing circuitry launches a particular application on system hardware based on the type of implantable medical device and the one or more actual electrode placement locations.

BRIEF DESCRIPTION OF THE DRAWINGS

The current technology may be more completely understood and appreciated in consideration of the following detailed description of various embodiments of the current technology in connection with the accompanying drawings.

DETAILED DESCRIPTION

Figure 1:
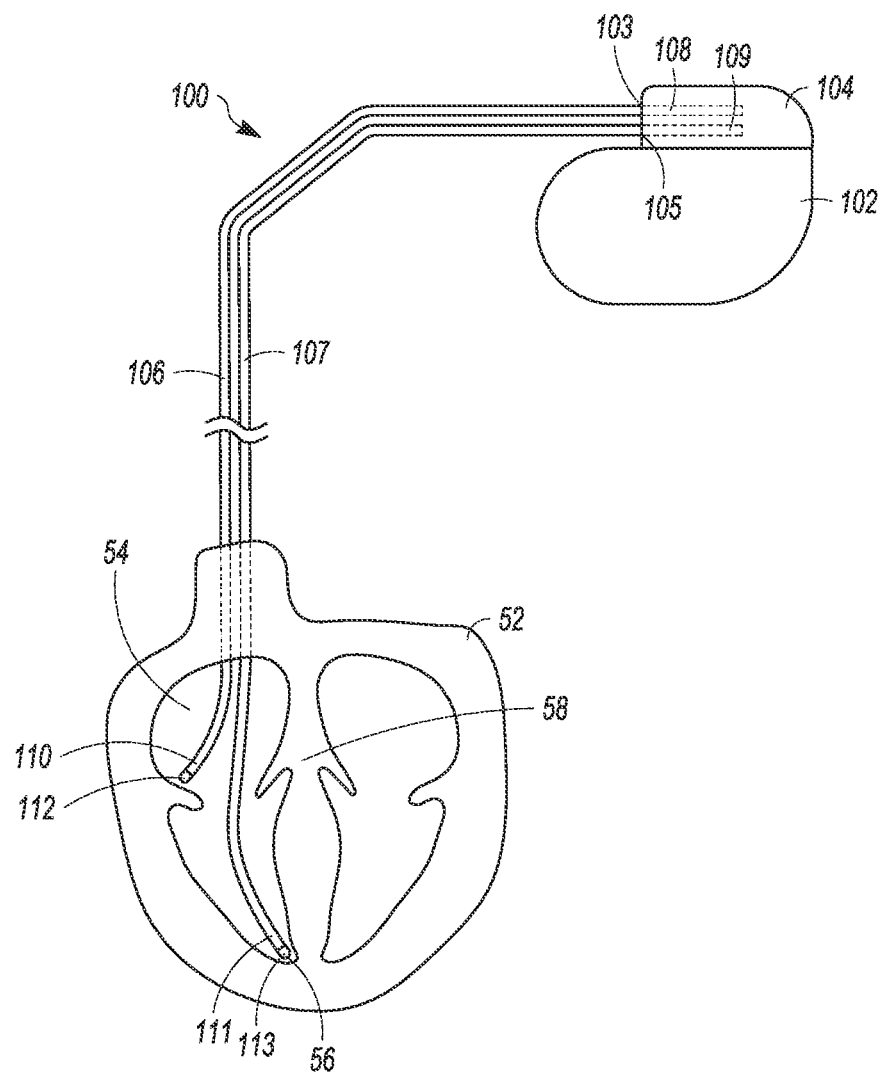
FIG. 1 is a schematic view of an implantable medical device 100 in a first configuration.

FIG. 1 is a schematic view of an implantable medical device 100 in a first configuration in accordance with some implementations of the technology disclosed herein. The implantable medical device 100 is generally configured to deliver electrical energy to a patient's heart 52, and has a pulse generator 102, a header 104, and one or more leads 106, 107. The leads 106, 107 each have a proximal end 108, 109 coupled to a port 103, 105 of the header 104 and a distal end 110, 111 extending into the heart 52. The distal ends 110, 111 of the leads 106, 107 define electrodes 112, 113 that are in electrical communication with the pulse generator 102 via the leads 106, 107.

In various embodiments, the implantable medical device 100 can be a cardiac rhythm management device, such as a pacemaker, a cardiac resynchronization therapy (CRT) device, a remodeling control therapy (RCT) device, a cardioverter/defibrillator, or a pacemaker-cardioverter/defibrillator. Other types of implantable medical devices 100 are certainly contemplated.

During the procedure of implanting the implantable medical device 100, the leads 106, 107 are generally threaded through a major vein (typically the subclavian vein) in the upper chest and into the heart with the help of imaging devices. The leads 106, 107 transvenously pass to the heart 52 and the electrodes 112, 113 are positioned at respective locations of the heart 52 that are intended to receive or sense electrical stimulus from a particular electrode 112, 113. Received and sensed electrical stimulus is generally recorded and saved by processing circuitry and memory in the pulse generator 102 for reporting to a user. In the current depiction, a first electrode 112 on a first lead 106 is positioned in the right atrium 54 of the heart 52 (typically the right atrial appendage), and a second electrode 113 on a second lead 107 is positioned at the right ventricle 56 apex of the heart 52. Other locations in the atrium or ventricle can also be used. While the current leads 106, 107 depicted each have a single electrode, in some embodiments multiple electrodes can be along the leads.

In a variety of implementations, once the electrodes 112, 113 are in the proper position, the proximal ends 108, 109 of the respective leads 106, 107 are attached to the pulse generator 102 via the header 104. Specifically, the proximal ends 108, 109 of the leads 106, 107 are inserted into respective ports 103, 105 in the header 104 and then secured in place. Typically, the header defines an atrial port 103 that is configured to receive the proximal end 108 of the lead that extends to the atrium, which is the first lead 106 in this example. Also, the header defines a ventricular port 105 that is configured to receive the proximal end 109 of the lead that extends to the ventricle, which is the second lead 107 in this example.

Following implantation, the physician can initialize the pulse generator 102 with a programmer. Programming instructions can be entered into the programmer via a user interface, which are transmitted to the pulse generator 102. In operation, the pulse generator 102 can collect data and generate pacing pulses or therapeutic shocks which are delivered to the heart 52 via the leads 106, 107.

The depiction in FIG. 1 is a schematic of a typical configuration of a pulse generator 102 after implantation in a patient. Because it is a typical configuration, pulse generators and their supporting software and hardware systems have been designed to reflect and support such a configuration. For example, various example pulse generators label each port 103, 105 to identify whether it is configured to receive the proximal end of an atrial or ventricular lead. An "A" label can indicate that the port is configured to receive an atrial lead, which refers to the lead having an electrode positioned in the atrium. A "V" can indicate that the port is configured to receive a ventricular lead, which refers to the lead having an electrode positioned in the ventricle. As such, data that is sensed through a particular port is recorded (and eventually reported to users) in the device with the same label as the port. This can introduce confusion when a physician elects to implant the electrodes 112, 113 of the pulse generator 102 in a non-typical configuration, such as that depicted in FIGS. 2 and 3, which will now be discussed.

Figure 2:
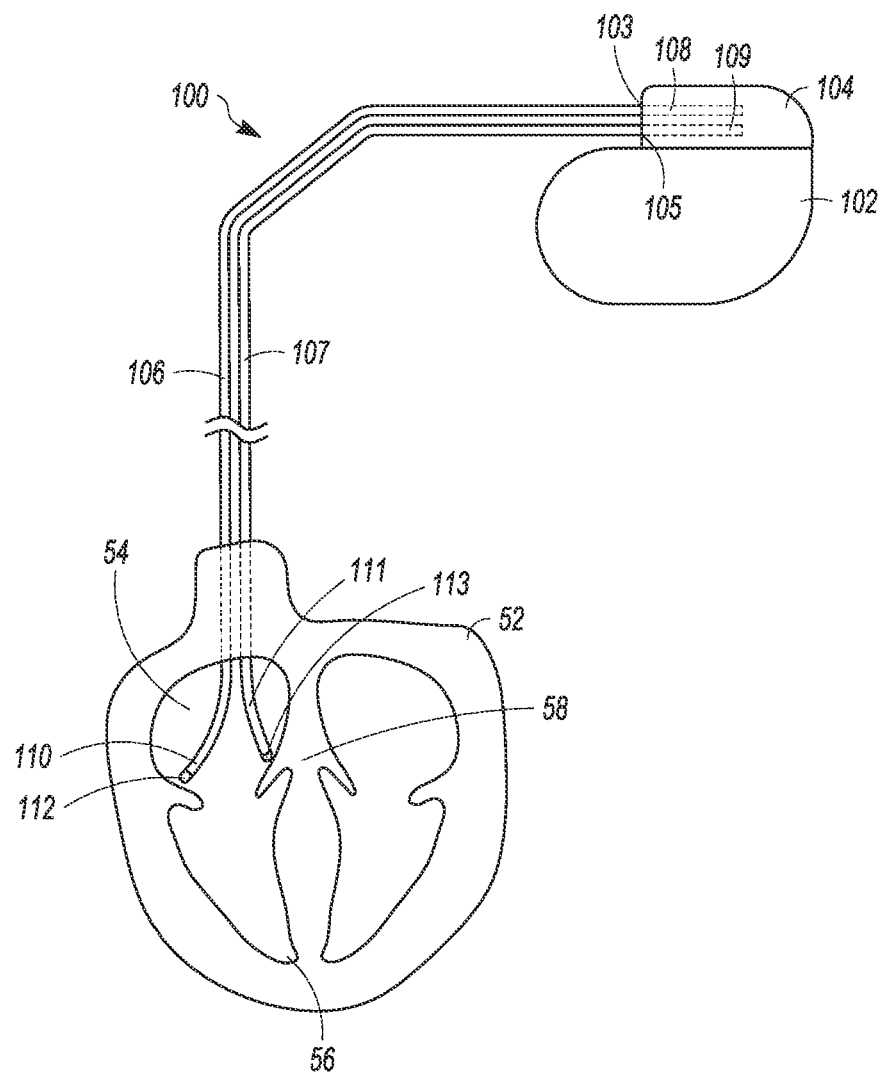
FIG. 2 is a schematic view of the implantable medical device 100 of FIG. 1 in a second configuration.

FIG. 2 is a schematic view of the implantable medical device 100 in a second configuration in accordance with some implementations of the technology disclosed herein. Similar to the configuration depicted in FIG. 1, here the first lead 106 extends from the first port 103 of the header 104 of the pulse generator 102 to the right atrium 54 of the heart 52, such that the first electrode 112 is positioned in the right atrium 54. However, unlike the previous configuration, the second lead 107 extends from the second port 105 to the His bundle 58 of the heart 52, such that the second electrode 113 is positioned in the His bundle 58. The second lead 107 extends to the His bundle through the atrial side of the tricuspid valve, in this example, but in some other examples the second lead 107 could extend to the His bundle 58 through the ventricular side of the tricuspid valve. When the second port 105 is identified as the ventricular port by the medical device, any data received from the second electrode 113 through the second lead 107 is recorded (and eventually displayed by a user output interface, as will be described below) as ventricular data, which can cause confusion when the data is being viewed and interpreted by caregivers and medical systems. The reason for this is because programming settings and physiological data from the His bundle is different than programming settings and physiological data from the right ventricle.

Figure 3:
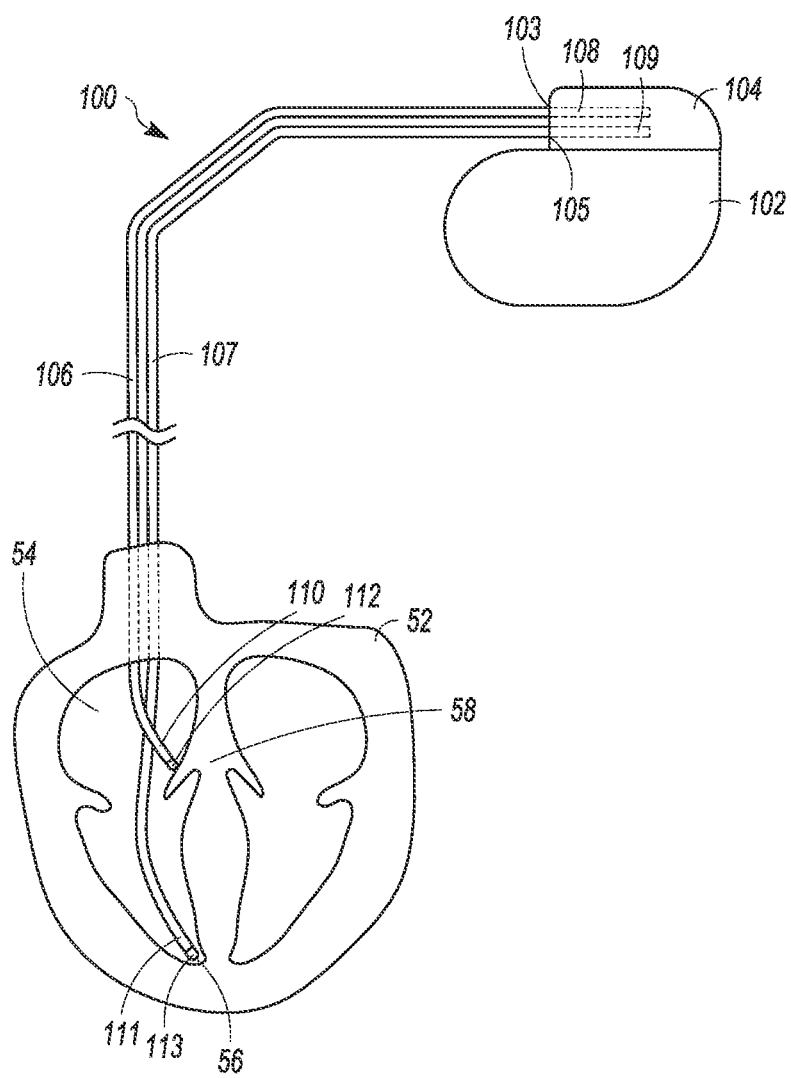
FIG. 3 is a schematic view of the implantable medical device 100 of FIG. 1 in a third configuration.

FIG. 3 is a schematic view of the implantable medical device 100 in a third configuration in accordance with some implementations of the technology disclosed herein. Similar to the configuration depicted in FIG. 1, here the second lead 107 extends from the second port 105 of the header 104 of the pulse generator 102 to the right ventricle 56 of the heart 52, such that the second electrode 113 is positioned in the right ventricle 56. However, unlike the configuration of FIG. 1, the first lead 106 extends from the first port 103 to the His bundle 58 of the heart 52, such that the first electrode 112 is positioned in the His bundle 58. When the first port 103 is identified as an atrial port by the medical device, any data received from the first electrode 112 through the first lead 106 is recorded and displayed as atrial data, which, again, can cause confusion when the data is being viewed and interpreted by caregivers and medical systems. Programming settings and physiological data from the His bundle is different than programming settings and physiological data from the right atrium.

It is noted that FIGS. 1-3 depict an example implantable medical device with two leads, but some medical devices consistent with the technology disclosed herein will incorporate three or even four leads. One alternate example implantable medical device, such as a CRT device, has three leads and defines a right atrial port, a right ventricular port, and a left ventricular port in the header. Similar to FIGS. 2-3, it can be possible to extend any of the leads to a different location in the patient's heart (such as the His bundle) than the location defined by the respective port label in the device. Table 1 below depicts some example electrode placement locations of various types of implantable medical devices.

TABLE 1

Example Lead Placement Locations

| Type of Device | 1st Electrode Location | 2nd Electrode Location | 3rd Electrode Location |
|---|---|---|---|
| Pacemaker | Atrium | Ventricle | N/A |
| | Atrium | His Bundle | N/A |
| | His Bundle | Ventricle | N/A |
| Implantable Cardioverter Defibrillator | Atrium | Right Ventricle | N/A |
| | His Bundle | Right Ventricle | N/A |
| CRT Pacemaker | Atrium | Right Ventricle | Left Ventricle |
| | Atrium | His Bundle | Left Ventricle |
| | Atrium | Left Ventricle | His Bundle |
| CRT Defibrillator | Atrium | Ventricle | His Bundle |
| | Atrium | His Bundle | Ventricle |

It should also be noted that the technology disclosed herein can also apply to leadless implantable medical devices, where electrodes that are not coupled to leads are implanted at locations in a patient's heart to sense physiological data and/or administer electrical therapy. In such embodiments, each electrode can be associated with a particular data channel of the medical device. In such embodiments, the data channel is not associated with a physical lead coupling the electrode to the medical device system through a particular port but, rather, is associated with a particular electrode and device that is implanted at a particular location. For example, a leadless pacemaker can be implanted in any of the four chambers of the heart, and more than one leadless pacer can be implanted in multiple chambers of the heart. One or more leadless pacers can communicate with, and send data to, a programmer or patient management system. Information about a leadless pacemaker's location can be important to correct programming and interpretation of data.

Figure 4:
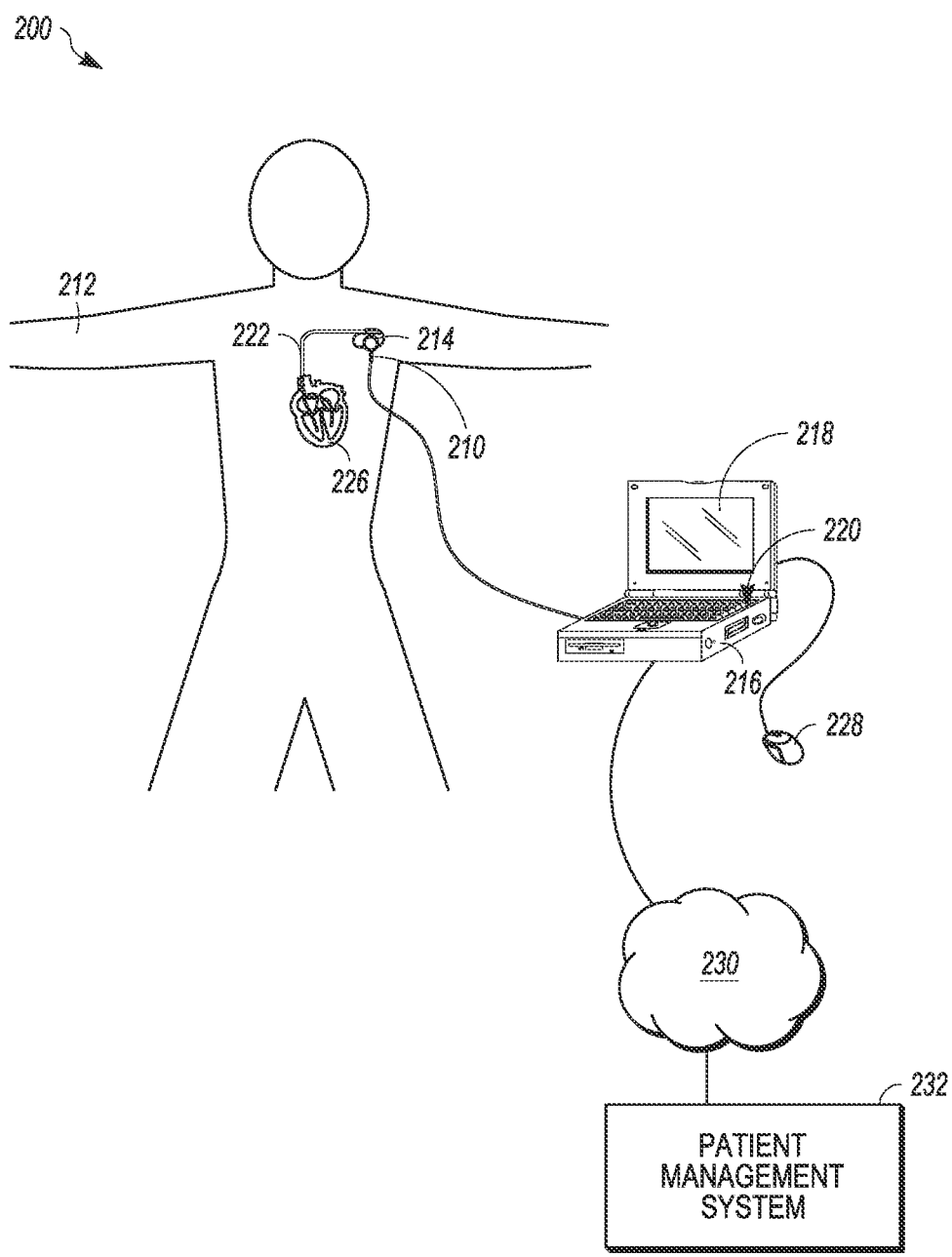
FIG. 4 is a schematic diagram of an exemplary implementation of a medical device system, consistent with the technology disclosed herein.

FIG. 4 is a schematic of an exemplary medical device system 200, consistent with some embodiments of the technology disclosed herein. The system 200 has an implantable medical device 214 implantable within a patient 212. The implantable medical device 214 can have pacing or other functionality. The implantable medical device 214 can be of various types such as, for example, a pacemaker, a cardioverter-defibrillator, a cardiac resynchronization device, or the like. The implantable medical device 214 has one or more electrodes 222 disposed in or near the patient's heart 226.

The implantable medical device 214 is configured for communication with an external programmer 216. The programmer 216 is also in communication with implantable sensor(s) of the implantable medical device 214, and/or one or more other implantable sensors. In some embodiments, communication between the implantable medical device 214 and the programmer 216 can be via inductive communication through a wand 210 held on the outside of the patient 212 near the implantable medical device 214. However, in other embodiments, communication can be carried out via radiofrequency transmission, acoustically, or the like. The implantable medical device 214 can be configured to store data over a period of time and periodically communicate with the programmer 216 in order to transmit some or all of the stored data.

As used herein, the term programmer 216 refers to a device that is capable of setting and modifying the operational parameters of an implantable medical device and records and displays data from implanted devices. In this context, the user of the programmer 216 is a clinician, physician or trained technician. The programmer 216 can be for example, a programmer, a programmer/recorder/monitor device, a computer, an advanced patient management system, a tablet, mobile phone, personal digital assistant (PDA), or the like. The programmer 216 can monitor physiological data from the implanted medical device 214 in some embodiments.

The programmer 216 generally has a user interface such as a keyboard 220, a mouse 228, a touch screen, or more than one such device to receive user input. The programmer 216 can also have a user output interface such as a video display 218 for displaying videos, user prompts, device operation parameters, settings, recommendations, and the like. In addition, the video display 218 can also be equipped with a touch screen, making it into a user input interface as well.

The programmer 216 can display real-time data transmitted from the implanted device such as ECG (electrocardiogram) signals, and/or stored data graphically, such as in charts or graphs, and textually through the video display 218. The programmer 216 can display parameters retrieved from the medical device 214 or calculated based on the parameters retrieved from the medical device 214. For example, the programmer 216 can display device operational parameters, patient indications relevant to the medical device 214, and the like. In at least one embodiment, programmer 216 can display system-recommended parameters that are formulated by the system. In various embodiments, consistent with the technology disclosed herein, the programmer 216 is further configured to display actual electrode placement locations of the medical device 214. The actual electrode placement locations can be determined based on data received from the implantable medical device 214. In some embodiments, the programmer 216 is configured to determine the electrode placement locations of the medical device 214 based on physiological data received from the medical device 214 and in other embodiments the programmer 216 is configured to determine the electrode placement locations based on electrode location data received from the medical device 214.

In addition, the programmer 216 can prompt a user for particular data. For example, prior to or immediately following implant of the implantable medical device 214, the user output interface 218 can prompt a user to enter in programming instructions to be transmitted to the implantable medical device 214. The user output interface 218 can also prompt the user to enter in the electrode 222 placement locations of the medical device 214. When the programmer 216 receives the electrode placement locations through the user input interface 220/228, the programmer can upload that data to the implantable medical device 214, where the electrode placement locations are stored for future interrogations of the implantable medical device 214.

In various embodiments, the programmer 216 is in communication with a patient management system 232. The patient management system 232 can additionally be in communication with electronic patient medical records in a variety of embodiments. The communication link 230 between the programmer 216 and the patient management system 232 may be via phone lines, the Internet, or any other data connection. In another embodiment, the programmer 216 is not in direct communication with a patient management system 232, but can be in indirect communication with the patient management system 232. In another embodiment, the programmer is not in communication with a patient management system 232.

Figure 5:
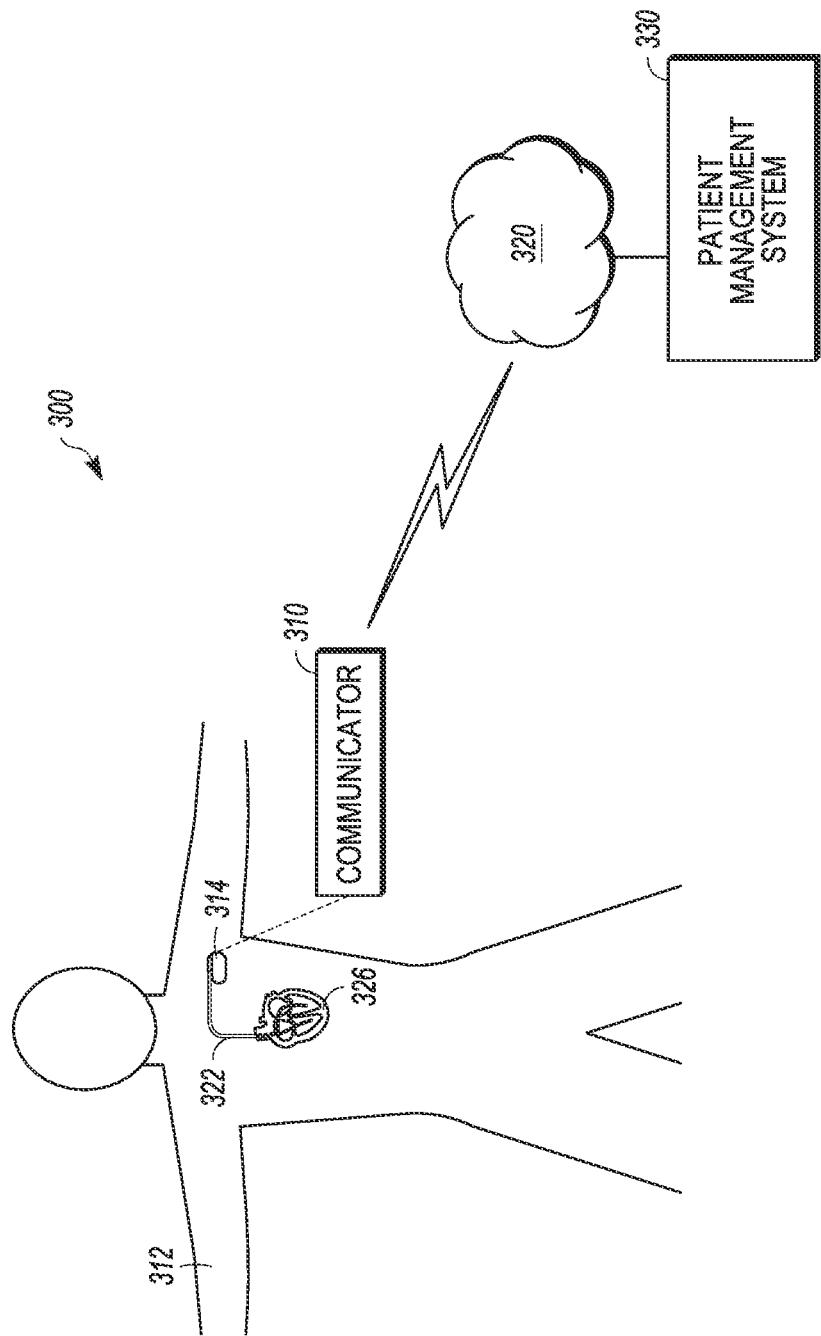
FIG. 5 is a schematic diagram of another exemplary implementation of a medical device system, consistent with the technology disclosed herein.

Now referring to FIG. 5, another example medical device system 300 is illustrated which is designed for use when the patient 312 is at a remote location from a patient management system 330 and caregivers are not physically present in the same space as the patient 312. For example, the patient 312 can be at his or her home while the clinician and the device programmer is at a hospital which is a few miles away or hundreds of miles away. The patient management system 330 is generally configured to receive and display similar information as the programmer, discussed above with respect to FIG. 4.

In the medical device system 300 of FIG. 5, a communicator 310 is at the location of the patient 312. The communicator 310 is generally configured to facilitate communication between the implantable medical device 314 and the patient management system 330. For example, the communicator 310 can transmit physiological data recorded by the implantable medical device 314 to the patient management system 330. Also, the communicator 310 can similarly transmit data, such as programming data, to the implantable medical device 314 from the patient management system 330. The communicator 310 is configured to be in communication with the implantable medical device 314. Communication between the communicator 310 and the implantable medical device 314 can be carried out by radiofrequency transmission, acoustically, or by inductive communication using a wand held on the outside of the patient 312 near the device 314.

The communicator 310 is also configured to be in communication with the patient management system 330. The communication link 320 between the communicator 310 and the patient management system 330 can be via phone lines, the Internet, or any other data connection, or a combination of different types of communication links. In various embodiments, the patient management system 330 can be accessed and viewed remotely on a user output interface by caregivers, for example via a computer with an internet connection, a hand-held mobile device, and the like. Such a configuration provides the health care provider or the patient the ability to receive and review implanted device data almost anywhere.

Figure 6:
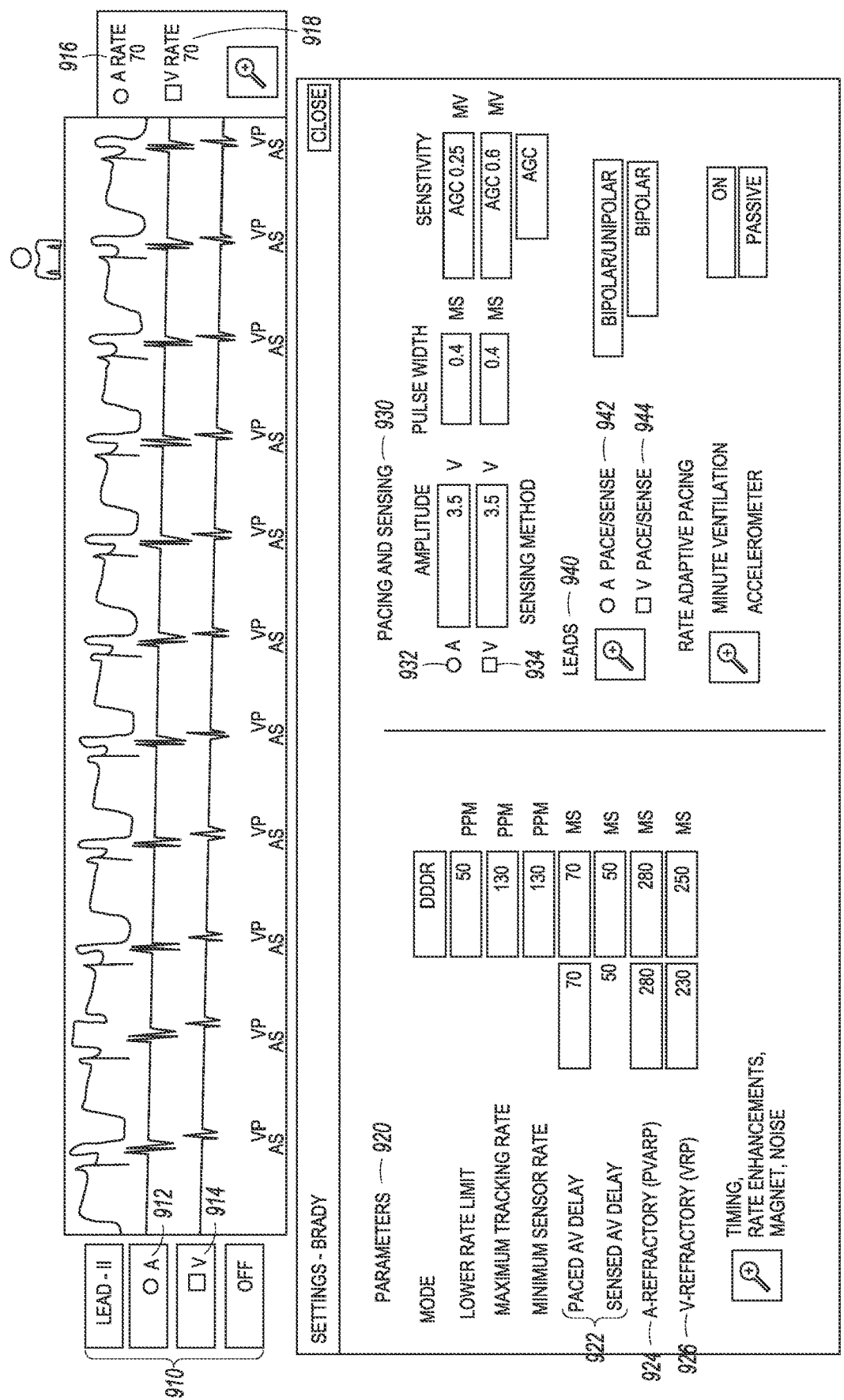
FIG. 6 is a representation of an example display of a user output interface consistent with some examples.

FIG. 6 is an example display of a user output interface 900 consistent with some examples. The user output interface 900 can be a component of systems described herein. In some examples, the user output interface 900 is the display screen of a programmer, such as a programmer described in conjunction with the description of FIG. 4. In some embodiments, the user output interface 900 is the display screen of a computer, such as a desktop computer, a laptop computer, a tablet, or a handheld device, where the computer is in communication with a patient management system, such as that described in the discussion of FIG. 5.

The user output interface 900 is generally configured to display data from the implanted medical device. A system (such as a programmer, a patient management system, or a monitoring device) receives data from the implanted medical device that defines the type of implantable medical device which selects the specific application that launches on the system to view the medical device data. The type of implanted medical device can be the make and model of the implanted medical device(s) or the category of implanted medical device, as examples. The specific application defines the display on the user output interface 900 such that the implanted medical device data can be displayed for the user and, in some instances, reprogrammed.

The current display of the user output interface 900 reflects ECG data 910 collected from the electrodes of the implanted medical device. Data from the atrial electrode is labeled "A" 912 and data from the ventricular electrode is labeled "V" 914, and markers 915 are shown that depict whether a physiological event was ventricular or atrial. Also, the atrial rate 916 and the ventricular rate 918 are denoted.

The user output interface 900 also reflects parameter settings 920 from the implantable medical device that includes, among other parameters, the paced and sensed AV delay 922, post-ventricular atrial refractory period 924, and the ventricular refractory period 926. Pacing and Sensing settings 930 are reported, which includes settings for the atrial electrode 932 and the ventricular electrode 934. Additionally, the type of electrode 940 at the atrial channel 942 and the ventricular channel 944 is reflected and reported.

As discussed above in the description of FIGS. 1-3, the implantable medical device labels data it records according to the port through which the data was received. As such, regardless of the actual placement of the electrodes, data retrieved from (or associated with) the atrial port is reflected as atrial data in the user output interface 900, and data retrieved from the ventricular port is reflected as ventricular data in the user output interface 900. If, for example, one of the electrodes is positioned in the His bundle instead of the atrium or ventricle, then a viewer would not know that based on the display screen, which can cause confusion and incorrect device programming.

Figure 7:
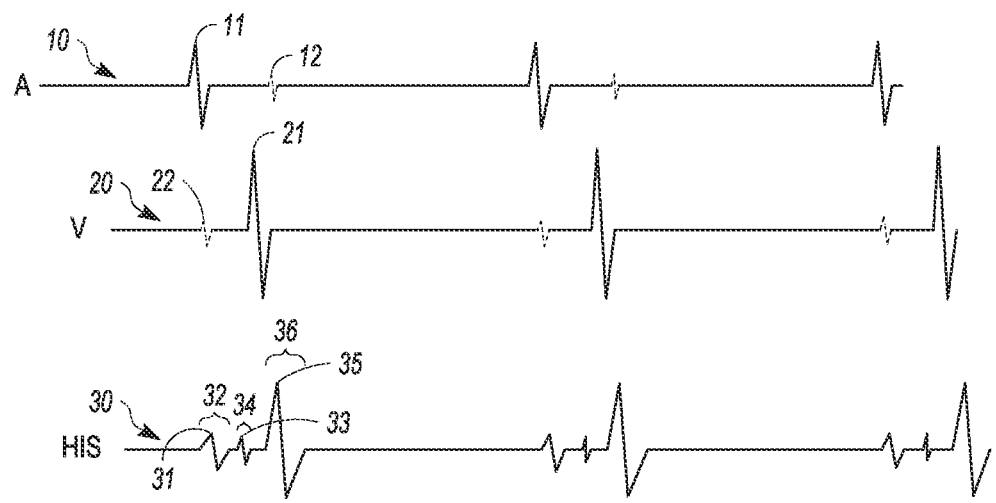
FIG. 7 is an example intracardiac electrogram.

For example, FIG. 7 depicts an example representative intracardiac electrogram reflecting atrial data 10, ventricular data 20, and His bundle data 30. The example electrogram is aligned to the atrial data 10, although relative timing may be different than that shown. The atrial data 10 reflects a far-field ventricular signal 12 and the ventricular data 20 reflects a far-field atrial signal 22 in this example, but typically such far-field deflections are not sensed by the implantable medical device due to cross-chamber blanking (e.g. once a detection occurs in the atrium, the ventricular signal is blanked to avoid oversensing a far-field atrial signal). The His bundle data 30 reflects an atrial component 32, a His bundle component 34, a ventricular component 36. The amplitude and timing of each component of the His signal data may vary considerably so a viewer could easily be confused if they did not explicitly know the signal data was from the His bundle.

The technology disclosed herein generally enables a system to identify the actual electrode placement within a patient's heart and reflect that information when reporting medical device data. In some embodiments, the electrode location information is entered and saved in the implantable medical device at the time of implant by the physician. In some other embodiments the system analyzes physiological data retrieved from the medical device to determine where the electrode is located in the patient's heart.

Figure 8:
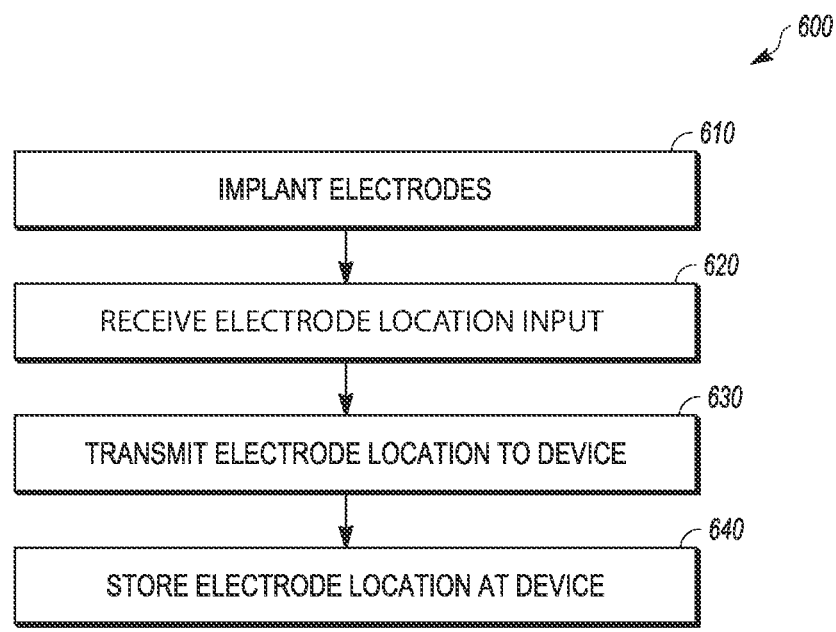
FIG. 8 is an example flow chart consistent with some examples of the current technology.

FIG. 8 is an example method 600 consistent with some examples. In this method 600, the medical device electrodes are implanted 610, a user input interface receives the actual electrode locations 620, the electrode location data is transmitted to the IMD 630, and the IMD stores the electrode location 640.

In some embodiments, the medical device electrodes are implanted 610 such that a distal end of the lead having the electrode extends to a location in a patient's heart, such as in systems similar to those described in accordance with FIGS. 1-3. In some other embodiments, such as with leadless medical devices, the electrodes are not coupled to leads. Upon or during implantation, which can be during an initialization step, a user input interface receives the actual electrode locations 620 of each of the electrodes. The actual electrode locations can be entered to correlate with a particular port of the IMD, or to a particular location of a leadless device. The user input interface can be on a programmer, for example, and the user can be a physician. In some embodiments, a user output interface displays a list of possible electrode locations for each of the electrodes, where the user chooses the actual electrode location from the possible electrode locations. In some other embodiments, the user types in the actual electrode locations through the user input interface. Possible electrode locations can include but are not limited to, for example, right atrium, left ventricle, right ventricle, His bundle, right ventricle apex, right ventricle septum, right ventricle outflow tract, and right atrial appendage.

Also during the initialization step, the actual electrode location data is transmitted to the implanted medical device 630. The programmer can transmit the electrode location data to the implanted medical device 630 through a medical device interface, for example. In such an embodiment, processing circuitry of the system can cause the medical device interface to upload the actual electrode placement locations to the implanted medical device upon receiving actual electrode placement locations by the user input interface. Other data can also be transmitted to the IMD, such as IMD settings and patient data.

The electrode location data is stored in the IMD 640. In devices having leads, the stored electrode location data will correlate the relevant port of the header in the IMD with the actual location of the electrode on the distal end of a particular lead. In leadless devices, the electrode location will typically correlate with the location of the leadless device. In some embodiments, the electrode location information is stored in binary code, although other data formats are possible. Generally the IMD is configured to permanently store the electrode location data.

Figure 9:
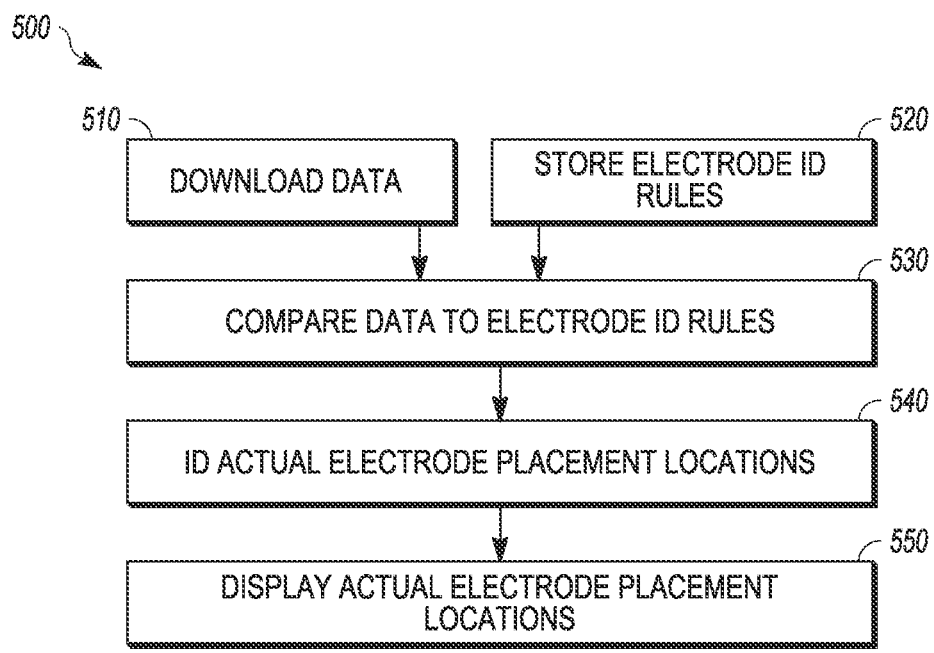
FIG. 9 is an example flow chart consistent with some embodiments of the technology described herein.

FIG. 9 is an example flow chart consistent with some embodiments of the technology described herein. Data is downloaded 510 from an implantable medical device and electrode location identification rules are stored 520. The data is compared to the electrode location identification rules 530 and the actual electrode placement locations are identified 540. The actual electrode placement locations are displayed 550.

The data is generally downloaded 510 by a medical device interface from an implanted medical device. The medical device interface can be a component of a programmer or other monitoring device, or a remote patient management system via a communicator, as examples. The data generally reflects patient physiological data. In some embodiments (such as those consistent with FIG. 8), the data can also reflect electrode location data that had been saved in the IMD.

Lead identification rules are generally stored 520 in the system to help identify the actual placement locations of electrodes of the IMD. The electrode location identification rules are generally stored in a memory. The electrode location identification rules 520 can define interpretation rules for reading actual electrode location data stored in the IMD (such as described in the discussion of FIG. 8). In some embodiments, the electrode location identification rules 520 is an algorithm that correlates the morphology of the patient physiological data with actual electrode placement locations.

The downloaded data is compared to electrode location identification rules 530 generally with processing circuitry of the system. As such, in some embodiments the patient physiological data is compared to an algorithm that correlates the morphology of the patient physiological data with actual electrode placement locations, and in other embodiments the electrode location data from the medical device is compared to the electrode location identification rules to interpret the actual electrode location data stored in the IMD.

Based on the comparison, the processing circuitry identifies one or more actual electrode placement locations 540 of the possible electrode placement locations of the implanted medical device.

A user output interface then displays the one or more actual electrode placement locations 550. In a variety of embodiments, the processing circuitry of the system causes the user output interface to display the actual electrode placement location 550. The user output interface generally has a display screen. In various embodiments the user output interface also displays a graphical representation of the downloaded data that reflects patient physiological data on the user output interface. The graphical representation of the downloaded data can be electrogram data, for example. In an example embodiment, the processing circuitry identifies an actual electrode placement location as in the His bundle. In such an embodiment, the user output interface can label the graphical representation of the downloaded data as His bundle data.

In various embodiments, the system also stores display definitions in a memory. Each display definition corresponds to a possible electrode placement location of the implanted medical device. As such, when the system identifies the actual electrode placement locations, the system also identifies corresponding display definitions.

Similarly, in various embodiments the system also stores possible programming options corresponding to various electrode placement locations. In such embodiments, the processing circuitry can identify the actual programming options of the possible programming options based on the identified actual electrode placement locations. The processing circuitry can cause the user output interface to display the actual programming options consistent with the one or more identified actual electrode placement locations.

Figure 10:
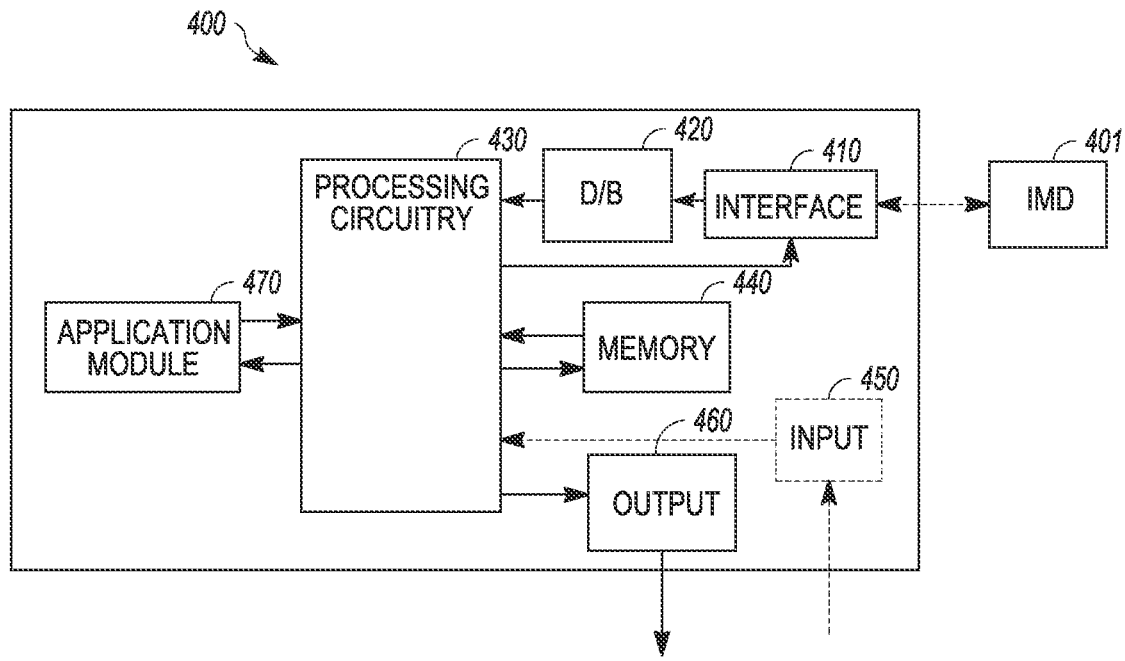
FIG. 10 is a schematic of an example system consistent with various embodiments of the technology disclosed herein.

FIG. 10 is a schematic of an example system consistent with various embodiments of the technology disclosed herein. The system 400 generally has a medical device interface 410, a database 420, memory 440, processing circuitry 430, a user input interface 450 and a user output interface 460. While the components of the system 400 are shown as a single device, it should be appreciated that the various components can be in more than one device.

The medical device interface 410 is generally configured to download data from an implanted medical device 401. The medical device interface 410 can incorporate short-range or long-range radio frequency telemetry circuitry or inductive telemetry circuitry, although other telemetry hardware is certainly contemplated. The downloaded data can be patient physiological data in various embodiments. Patient physiological data can be electrogram data, for example. In some embodiments the downloaded data can also include electrode location data that is stored in the implanted medical device. In some embodiments the medical device interface 410 is also configured to upload data to an implanted medical device 401. For example, the medical device interface 410 can be configured to reprogram the implanted medical device 401.

The database 420 is generally configured to receive the downloaded data from the implanted medical device 401. In some embodiments the database 420 temporarily stores the downloaded data from the implanted medical device 401 for use by the system 400 in displaying and analyzing the data. The memory 440, while shown separately from the database 420, can be the same component as the database in some embodiments. The memory 440 is generally configured to store electrode location identification rules and display definitions. Each of the display definitions correspond to possible electrode placement locations of the implanted medical device. The memory can also be configured to store possible programming options corresponding to various electrode placement locations.

The processing circuitry 430 is generally configured to compare the downloaded data (in the database 420) from the implanted medical device 401 to electrode location identification rules stored in the memory 440 to identify one or more actual electrode placement locations—also stored in the memory 440—of the possible electrode placement locations of the implanted medical device 401. In some embodiments, the processing circuitry 430 is configured to interpret electrode location data that was downloaded from the implanted medical device 401 using the electrode location identification rules. The electrode location data can be data that was programmed into the implanted medical device at the time of implantation, consistently with the discussion of FIG. 8. In such embodiments the electrode location identification rules are interpretation rules that the processing circuitry 430 is configured to apply to the electrode location data.

In some embodiments, the electrode location identification rules in the memory 440 is an algorithm that correlates the morphology of the physiological data with actual electrode placement locations. In such embodiments, the processing circuitry 430 is configured to compare the patient physiological data in the database 420 to the algorithm. For example, the processing circuitry 430 is configured to identify if an actual electrode placement location as His bundle based on the morphology of the patient's physiological data, which will be described in more detail in the discussion of FIGS. 12 and 13, below.

The user output interface 460 is in communication with the processing circuitry 430. The user output interface 460 can be a display, in various embodiments, as has been described herein. Among other data, the user output interface 460 is generally configured to display a graphical representation of the downloaded data in the database 420, such as the currently programmed parameters and patient physiological data. The user output interface 460 is configured to label the graphical representation of the downloaded data with the actual electrode placement locations.

The processing circuitry 430 is configured to cause the user output interface 460 to display the one or more actual electrode placement locations. In some embodiments, the processing circuitry 430 is configured to identify actual programming options of the possible programming options based on the actual electrode placement locations. In various embodiments, the processing circuitry 430 is configured to cause the user output interface to display the actual programming options consistent with the one or more actual electrode placement locations.

The processing circuitry 430 can cause the user output interface 460 to display the one or more actual electrode placement locations in a number of ways. Generally, the processing circuitry 430 is in communication with an application module 470. The application module 470 stores the specific applications that automatically launch in response to the system downloading data from the implanted medical device 401. In some examples, upon receipt of the downloaded data, the processing circuitry 430 identifies the type of implanted medical device 401 and the one or more actual electrode placement locations, which identifies a specific application. Upon identification of the application, the processing circuitry 430 launches the specific application on system hardware and causes the user output interface 460 to display the output of the application, which inherently displays the one or more actual electrode placement locations.

In some other examples, the processing circuitry 430 identifies the type of implanted medical device 401, which identifies the specific application. Upon further identifying the one or more actual electrode placement locations, the processing circuitry 430 launches the application on system hardware and modifies the labels in the application output such that the user output interface 460 correctly displays the one or more actual electrode placement locations. Other approaches are also contemplated.

In some embodiments, where the system 400 is a programmer, for example, there can be a user input interface 450 that is in communication with the processing circuitry 430. As discussed above with reference to FIG. 8, the user input interface 450 can be configured to receive actual electrode placement locations of the implanted medical device upon implantation. In such an example, the processing circuitry 430 is configured to cause the medical device interface 410 to upload the actual electrode placement locations to the implanted medical device 401 upon receiving actual electrode placement locations by the user input interface 450.

Figure 11:
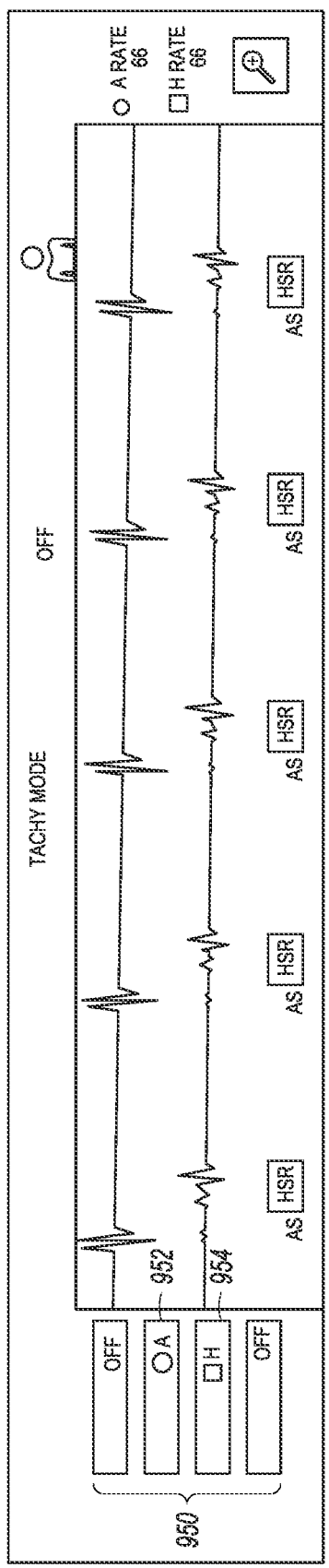
FIG. 11 is a representation of an example display of a user output interface consistent with some examples.
Figure 11:
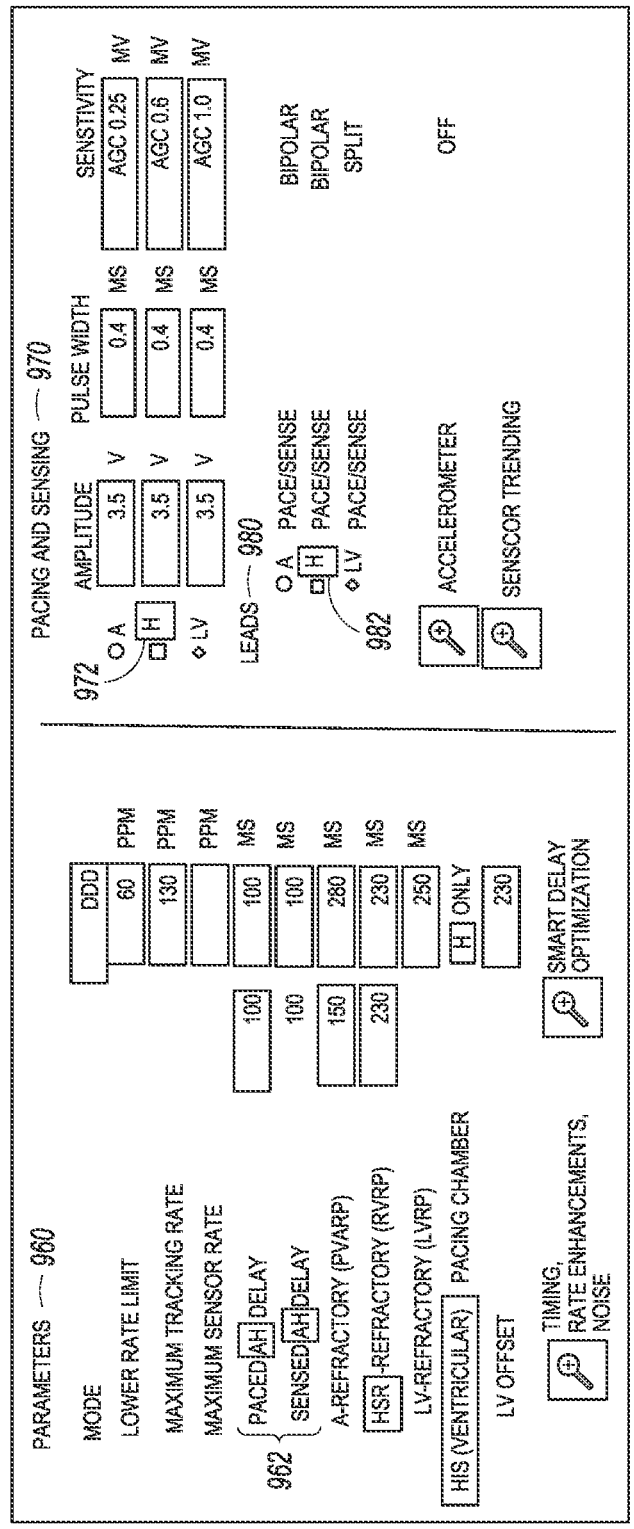

FIG. 11 is a representation of another example display 901 of a user output interface consistent with some example implementations of the currently-described technology. The application display is consistent with a CRT device. Prior to the currently described technology, upon identification of the type of implanted medical device in communication with the system, an application would automatically launch, which would display atrial electrode data, right ventricular electrode data, and left ventricular electrode data regardless of the actual electrode placement. In this example, however, a system disclosed herein has identified an atrial electrode, a His bundle electrode, and a left ventricular electrode as the one or more actual electrode placement locations. As a result, the display 901 of the user output interface reflects the one or more actual electrode placement locations and labels the data appropriately.

For example, the electrogram data 950 reflects atrial data 952 and His bundle 954 data. In some embodiments the electrogram data 950 associated with the His bundle 954 can be annotated and labeled by the system to reflect the atrial, ventricular, and His bundle components, which are depicted in FIG. 8. Furthermore, the actual programming options based on the actual electrode placement locations are displayed, such as the paced and sensed AH delay 962 in the parameter settings 960, the His bundle 972 pacing and sensing settings 970, and the reflection of the His bundle electrode 982 in the lead settings 980. As discussed above, the display 901 can be a result of a modification of the output of a specific application launched, or it can be a particular application launched in response to identification of the type and the actual electrode placement locations of implanted medical device.

Figure 12:
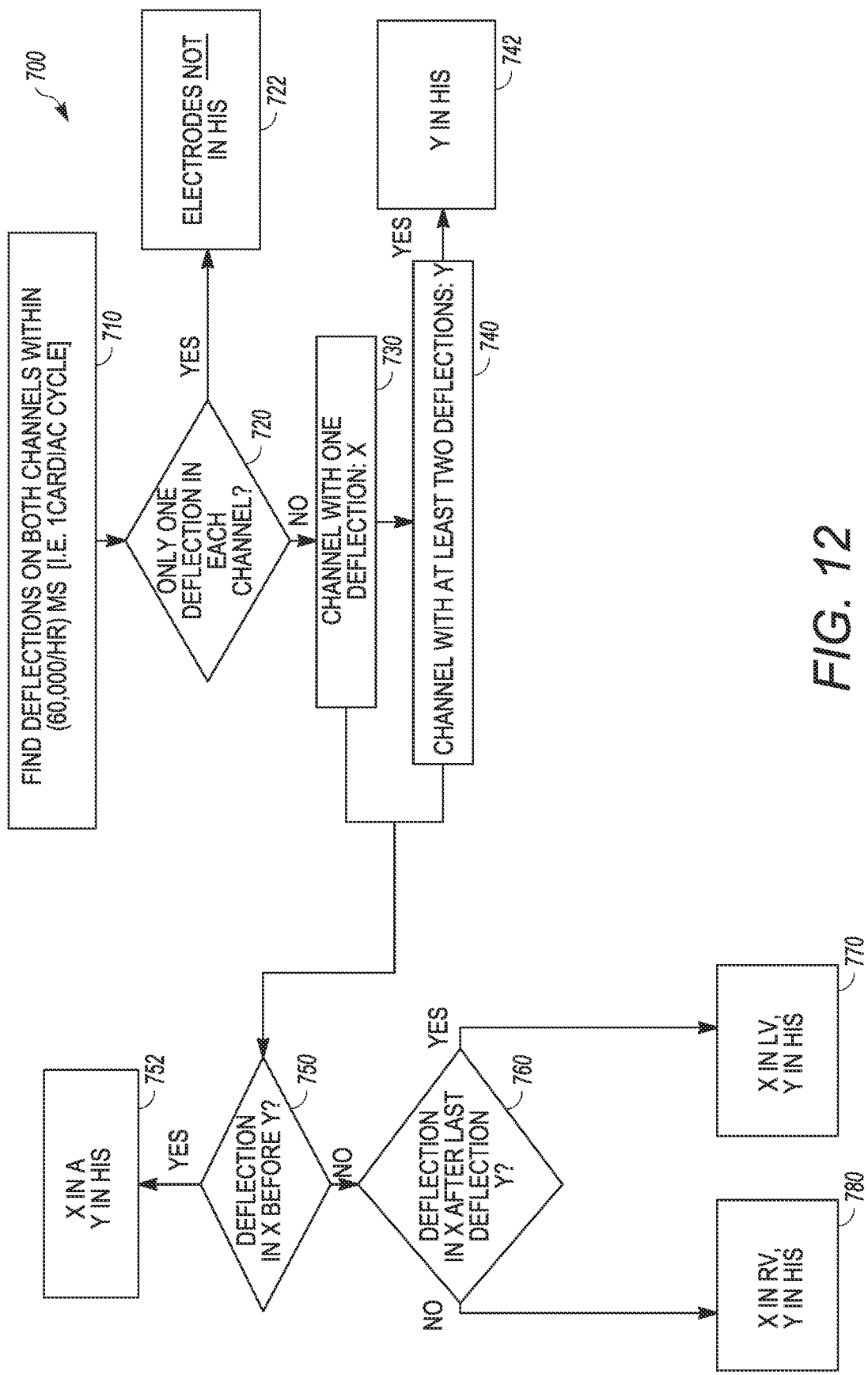
FIG. 12 is an example method consistent with some embodiments.

FIG. 12 is an example method consistent with some embodiments. The present example is consistent with an algorithm that can be implemented by processing circuitry of a programmer to identify the actual electrode placement locations of an implanted medical device. This example is relevant to medical device that has two channels of data. The system is generally configured to disregard data on a particular channel that is the result of far-field sensing, such as through blanking, described above in the discussion of FIG. 7, or through an alternative approach.

The system identifies a deflection on each channel within a single cardiac cycle 710. A cardiac cycle is generally considered to be equal to, in milliseconds, 60,000 divided by the heart rate. A deflection can be defined as a sensor reading that exceeds a certain threshold with respect to, for example, amplitude, polarity, or frequency. In some embodiments, a deflection is defined as a peak sensor value with a maximum amplitude that occurs within a 30 ms window of time on a particular channel, such as peaks 11, 21, 31, 33, and 35 identified in FIG. 7. In some embodiments, a deflection is defined as a negative peak with a minimum amplitude that occurs within a 30 ms window of time of a particular channel.

If the system identifies only a single deflection in each channel 720, such as reflected in the atrial data 10 and the ventricular data 20 of FIG. 7, then the system determines that neither of the electrodes are located at the His bundle 722. However, if there is a channel Y with at least two deflections 740 and a channel X with a single deflection 730, then the system identifies the electrode associated with channel Y as being located at the His bundle 742. To determine where the electrode associated with channel X is positioned, the system analyzes where the deflection in channel X occurs relative to the deflections of channel Y. If the channel X deflection occurs before the channel Y deflections 750, the system concludes that the electrode associated with channel X is positioned in the atrium 752. If the deflection in channel X is after the last deflection in channel Y 760, then the system concludes that the electrode associated with channel X is located in the left ventricle 770. If the deflection in channel X is not after the last deflection in channel Y 760, then the system concludes that the electrode associated with channel X is located in the right ventricle 780.

Figure 13:
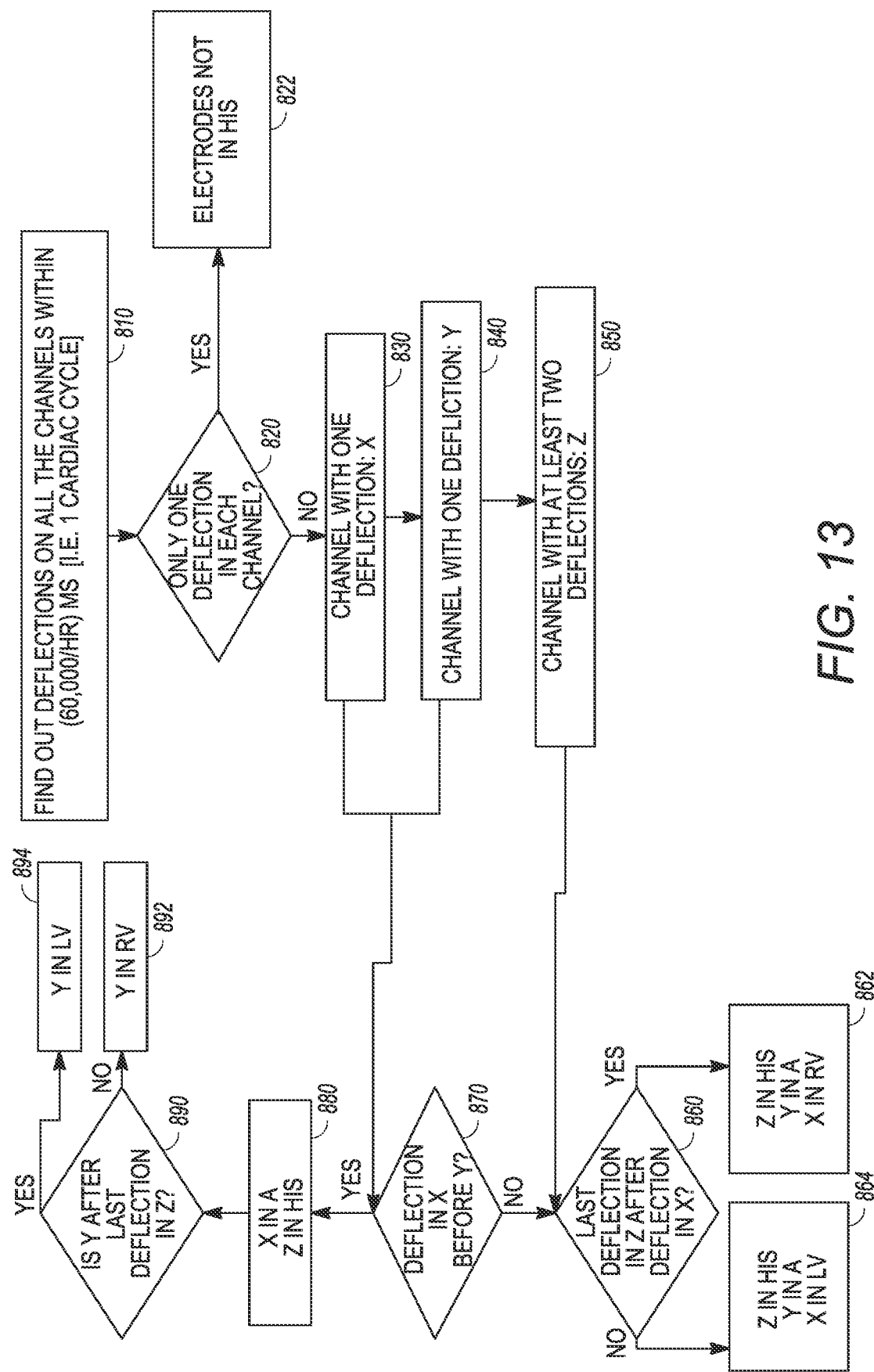
FIG. 13 is another example method consistent with some embodiments.

FIG. 13 is example of another method consistent with some embodiments. The present example is consistent with another algorithm that can be implemented by processing circuitry of a programmer to identify the actual electrode placement locations of an implanted medical device. In this example, there are three channels of data X, Y, and Z associated with three electrodes of the medical device system. Similar to the method above, the system is configured to disregard data on a particular channel that is the result of far-field sensing.

The system identifies a deflection on each channel within a single cardiac cycle 810. If there is only one deflection in each channel 320, then the system concludes that none of the electrodes associated with each of the channels is located in the His bundle 822. Otherwise, a channel X is identified as having one deflection 830, a channel Y is identified as having one deflection 840, and a channel Z is identified as having at least two deflections 850. The deflections of channels X and Y are compared relative to each other, and if the deflection in channel X occurs before the deflection in channel Y 870, then the system determines than the electrode associated with channel X is positioned in the atrium and the electrode associated with channel Z is positioned at the His bundle 880. The system also analyzes whether the deflection in channel Y is after the last deflection in channel Z 890. If so, the system determines that the electrode associated with channel Y is positioned in the left ventricle 894. Otherwise, the system determines that the electrode associated with channel Y is positioned in the right ventricle 892.

If the deflection in channel X does not occur before the deflection in channel Y 870, then the system evaluates whether the last deflection in channel Z occurs after the deflection in channel X 860. If so, the system determines that the electrode associated with channel Y is positioned in the atrium, the electrode associated with channel X is positioned in the right ventricle, and the electrode associated with channel Z is positioned in the His bundle 862.

Figure 14:
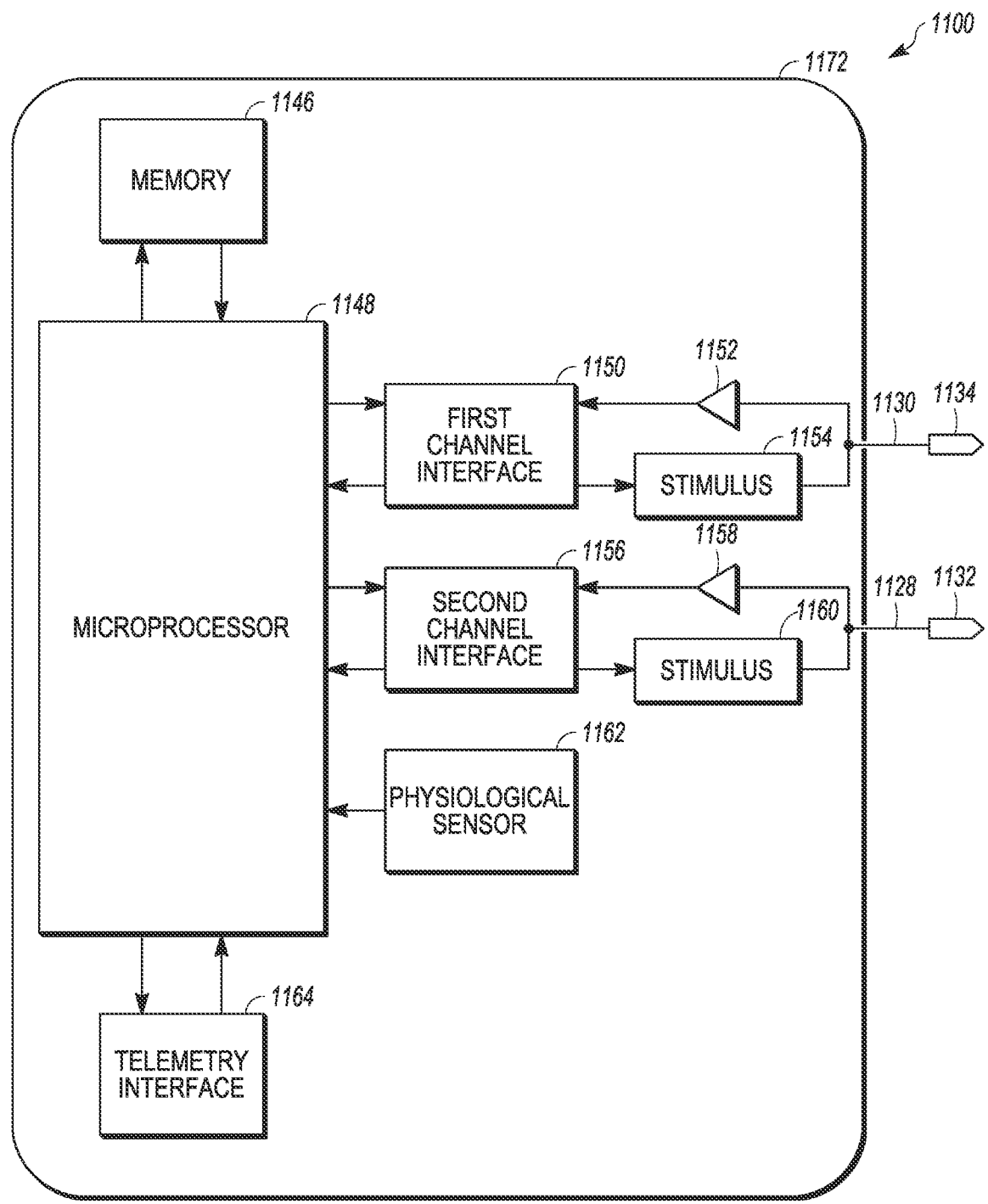
FIG. 14 is a schematic diagram of an example implantable medical device consistent with the technology disclosed herein.

FIG. 14 is a schematic view of components of an implantable medical device in accordance with embodiments of the current technology. The implantable medical device 1100 can have a device housing 1172 containing various components and one or more stimulation leads 1130, 1128 extending from the housing 1172. The implantable medical device 1100 can also have physiological sensors 1162 in addition to the leads 1130, 1128.

The implantable medical device 1100 can include a microprocessor 1148 (or processor) that communicates with a memory 1146 via a bidirectional data bus. The memory 1146 typically includes ROM and/or RAM for program storage and RAM for storage of physiological data. The memory 1146 can further be configured to permanently store data such as electrode location data that can be uploaded to the implantable medical device 1100, such as described above. The implantable medical device 1100 can be configured to execute various operations such as processing and recording signals and administering therapy described herein. A telemetry interface 1164 is also provided for communicating with external systems, such as programmers, monitoring systems, patient management systems, or other systems.

The implantable medical device 1100 can have first sensing and pacing channels including a first sensing amplifier 1152, a first output circuit 1154, and a first channel interface 1150 which communicates bidirectionally with a port of the microprocessor 1148. The first sensing and pacing channel can be in communication with a first stimulation lead 1130 and a first electrode 1134. The implantable medical device 1100 can have a second sensing and pacing channel including a second sensing amplifier 1158, a second output circuit 1160, and a second channel interface 1156 which communicates bidirectionally with a port of the microprocessor 1148. The second sensing and pacing channel can be in communication with a second stimulation lead 1128 and second electrode 1132. For each channel, the same lead and electrode can be used for both sensing and pacing. The channel interfaces 1150, 1156 can include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers.

In some embodiments, a physician can input the electrode location data for the first electrode 1134 in communication with the first channel and the second electrode 1132 in communication with the second channel. Such electrode location data can be received by a programmer during or upon implantation of the implantable medical device 1100. This example is discussed in detail with respect to FIG. 8. As mentioned above, in some embodiments the technology disclosed herein can be implemented in a leadless medical device, where an electrode is not coupled to the distal end of a lead but, rather, is coupled to the housing of the device, which is implanted at a particular location. In such an example, multiple leadless devices each having one or more electrodes can be implanted in different locations in a patient's heart.

It should also be noted that, as used in this specification and the appended claims, the phrase "configured" describes a system, apparatus, or other structure that is constructed to perform a particular task or adopt particular characteristics. The phrase "configured" can be used interchangeably with other similar phrases such as "arranged", "arranged and configured", "programmed" "constructed and arranged", "constructed", "manufactured and arranged", and the like. Various steps of the processes disclosed and described herein can be stored as program instructions on a non-transitory computer-readable storage medium that are configured to be executed by a processor.

All publications and patent applications in this specification are indicative of the level of ordinary skill in the art to which the present technology pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive.

What is claimed is:

1. A medical device system comprising:
    telemetry circuitry adapted to download data from an implanted medical device that comprises electrodes implanted in a patient's heart, wherein the downloaded data comprises a first data channel and a second data channel, wherein each data channel is associated with a particular electrode of the implanted electrodes, wherein each data channel comprises electrode data from the patient's heart sensed by the electrode associated with the data channel;
    a memory storing:
        a first expected deflection pattern over a single cardiac cycle corresponding to a first possible electrode placement location;
        a second expected deflection pattern over a single cardiac cycle corresponding to a second possible electrode placement location; and
        electrode location identification rules, wherein the electrode location identification rules comprise an algorithm to identify measured deflections of electrode data and to correlate the measured deflections of the electrode data from each data channel of the implanted medical device with the first expected deflection pattern and the second expected deflection pattern;
    processing circuitry configured to execute the algorithm comprising:
        identifying one or more measured deflections in the electrode data for each data channel over a single cardiac cycle;
        determining an actual electrode placement location for each data channel based on which of the expected deflection patterns best correlates with a number of deflections and a timing of deflections of the measured deflections over the single cardiac cycle for each data channel;
        based on the determining, assigning one of the first or second possible electrode placement locations as an actual electrode placement location for the first data channel, and the other of the first or second possible electrode placement location as a second actual electrode placement location for the second data channel; and causing a user output interface to display the actual electrode placement locations.

2. A medical device system of claim 1, wherein the user output interface is configured to display a graphical representation of the electrode data from the patient's heart.

3. A medical device system of claim 1, wherein the possible electrode placement locations comprise atrium, right atrium, left ventricle, right ventricle, and His bundle, and wherein the memory stores an expected deflection pattern for each of the possible electrode placement locations.

4. A medical device system of claim 1, further comprising a user input interface in communication with the processing circuitry, wherein the user input interface is configured to receive user-input electrode placement locations of the implanted medical device upon implantation, and the processing circuitry is configured to cause the medical device interface to upload the user-input electrode placement locations to the implanted medical device upon receiving user-input electrode placement locations by the user input interface.

5. A medical device system of claim 1, wherein the memory further stores possible programming options corresponding to various electrode placement locations and wherein the processing circuitry is further configured to identify actual programming options of the possible programming options based on the actual electrode placement locations, and cause the user output interface to display the actual programming options consistent with the one or more actual electrode placement locations.

6. A medical device system of claim 1, wherein the downloaded data reflects a type of implanted medical device and the processing circuitry is configured to launch an application on the system based on the downloaded data, and the processing circuitry is further configured to cause the user output interface to display the actual electrode placement locations by modifying the launched application.

7. A medical device system of claim 1, wherein the downloaded data comprises a type of implanted medical device, and wherein the type of implanted medical device and the one or more actual electrode placement locations define an application to launch on the system.

8. A medical device system of claim 3, the algorithm further comprising assigning a first electrode associated with the first data channel to an actual electrode placement location of the His bundle if the number and timing of the measured deflections of the first data channel best correlates with the expected deflection pattern of the His Bundle.

9. A medical device system of claim 3, wherein a deflection is defined as a value of the electrode data that exceeds a certain threshold with respect to amplitude, and wherein the expected deflection pattern for the His Bundle comprises at least two deflections.

10. A medical device system of claim 9, the algorithm further comprising assigning a first electrode associated with the first data channel to an actual electrode placement location of the His bundle if the electrode data from the first data channel comprises two deflections within a single cardiac cycle and the electrode data from the second data channel comprises one deflection within a single cardiac cycle.

11. A medical device system of claim 9, the algorithm further comprising assigning none of the electrodes to an actual electrode placement location of the His Bundle if the electrode data from all the associated data channels comprise a single deflection within a single cardiac cycle.

12. A method comprising:
downloading data, by a medical device interface adapted to download the data from an implanted medical device that comprises electrodes implanted in a patient's heart, the downloaded data comprising a first data channel and a second data channel, wherein each data channel is associated with a particular electrode of the implanted electrodes, wherein each data channel comprises electrode data from the patient's heart sensed by the electrode associated with the data channel;

storing a first expected deflection pattern over a single cardiac cycle corresponding to a first possible electrode placement location, a second expected deflection pattern over a single cardiac cycle corresponding to a second possible electrode placement location, and electrode location identification rules in memory, wherein the electrode location identification rules comprise an algorithm to identify deflections of electrode data and to correlate the deflections of electrode data from each data channel of the implanted medical device with the first expected deflection pattern and the second expected deflection pattern; and executing the algorithm with processing circuitry, the algorithm comprising:
identifying one or more deflections in the electrode data for each data channel within a single cardiac cycle;
determining an actual electrode placement location for each data channel based on which of the expected deflection patterns best correlates with a number of deflections and a timing of deflections of the identified deflections over the single cardiac cycle for each data channel;

based on the determining, assigning one of the first or second possible electrode placement locations as an actual electrode placement location for the first data channel, and the other of the first or second possible electrode placement location as a second actual electrode placement location for the second data channel; and causing a user output interface to display the determined actual electrode placement locations.

13. The method of claim 12, further comprising displaying a graphical representation of the electrode data from the patient's heart on the user output interface.

14. The method of claim 12, further comprising storing expected deflection patterns for each of atrium, right atrium, left ventricle, right ventricle, and His bundle, in the memory.

15. The method of claim 14, further comprising identifying, by the processing circuitry, an actual electrode placement location as the His bundle, and further comprising labeling, by the user output interface, the graphical representation of the downloaded data as His bundle data.

16. The method of claim 12, further comprising receiving, by a user input interface, user-input electrode placement locations of the implanted medical device upon implantation, and the processing circuitry causing the medical device interface to upload the user-input electrode placement locations to the implanted medical device upon receiving user-input electrode placement locations by the user input interface.

17. The method of claim 12, further comprising storing, in the memory, possible programming options corresponding to various electrode placement locations; identifying, by the processing circuitry, actual programming options of the possible programming options based on the actual electrode placement locations; and the processing circuitry causing the user output interface to display the actual programming options consistent with the one or more actual electrode placement locations.

18. The method of claim 12, further comprising the processing circuitry launching a particular application on system hardware based on a type of implanted medical device and modifying labels in an output of the particular application to reflect the one or more actual electrode placement locations.

19. The method of claim 12, further comprising processing circuitry launching a particular application on system hardware based on a type of implanted medical device and the one or more actual electrode placement locations.

20. A medical device system comprising:
    telemetry circuitry adapted to download data from an implanted medical device that comprises electrodes implanted in a patient's heart, the downloaded data comprising a first data channel and a second data channel, wherein each data channel is associated with a particular electrode of the implanted electrodes, wherein each data channel comprises electrode data from the patient's heart sensed by the electrode associated with the data channel;
    a memory storing:
        a first expected deflection pattern over a single cardiac cycle corresponding to a first possible electrode placement location;
        a second expected deflection pattern over a single cardiac cycle corresponding to a second possible electrode placement location; and
        electrode location identification rules, wherein the electrode location identification rules comprise an algorithm to identify deflections of electrode data and to correlate the deflections of electrode data from each data channel of the implanted medical device with the first expected deflection pattern and the second expected deflection pattern;
    processing circuitry configured to execute the algorithm comprising:
        identifying one or more deflections in the electrode data for each data channel within a single cardiac cycle;
        determining an actual electrode placement location for each data channel based on which of the expected deflection patterns best correlates with a number of deflections and a timing of deflections of the identified deflections over the single cardiac cycle for each data channel;
    based on the determining, assigning one of the first or second possible electrode placement locations as an actual electrode placement location for the first data channel, and the other of the first or second possible electrode placement location as a second actual electrode placement location for the second data channel;
    causing a user output interface to display the determined actual electrode placement locations; and
    launching an application on system hardware based on a type of implanted medical device and modifying labels in an output of the application to reflect the one or more actual electrode placement locations.

* * * * *